United States Patent [19]

Nishi

[11] Patent Number: 4,617,018
[45] Date of Patent: Oct. 14, 1986

[54] IRRIGATING CANNULA FOR EXTRACTING LENS NUCLEUS FOR USE IN EXTRACAPSULAR CATARACT EXTRACTION

[76] Inventor: Okihiro Nishi, 3377, Oaza Hoshida, Katano-shi, Osaka, Japan

[21] Appl. No.: 602,843

[22] Filed: Apr. 23, 1984

[30] Foreign Application Priority Data

Nov. 18, 1983 [JP] Japan .................................. 58-218377

[51] Int. Cl.4 ...................... A61M 5/325; A61M 25/00
[52] U.S. Cl. ....................................... 604/264; 604/117
[58] Field of Search ..................... 604/22, 27, 30, 264, 604/117, 150, 290, 298, 300, 302, 294–297, 299, 301, 73, 272, 275; 128/305, 244, 303 R, 304, 348.1

[56] References Cited

U.S. PATENT DOCUMENTS

| | | | |
|---|---|---|---|
| 2,117,312 | 5/1938 | Gauly | 128/303 R |
| 2,153,417 | 4/1939 | Gauly | 604/294 |
| 3,481,338 | 12/1969 | Sobel et al. | 604/264 |
| 4,239,045 | 12/1980 | Schlein | 128/305 |
| 4,301,802 | 11/1981 | Poler | 604/22 |
| 4,331,130 | 5/1982 | Lewicky | 604/294 |
| 4,468,218 | 8/1984 | Armstrong | 604/264 |
| 4,479,802 | 10/1984 | Anis | 604/275 |

FOREIGN PATENT DOCUMENTS

| | | | |
|---|---|---|---|
| 629923 | 10/1978 | U.S.S.R. | 128/303 R |
| 735254 | 6/1980 | U.S.S.R. | 128/304 |
| 753434 | 8/1980 | U.S.S.R. | 604/27 |
| 1009449 | 4/1983 | U.S.S.R. | 128/305 |

OTHER PUBLICATIONS

Catalogue "Gamut of Cannulas", publisher: Instrument Company, published date: Mar. 1980.

Primary Examiner—Dalton L. Truluck
Assistant Examiner—Mario Costantino
Attorney, Agent, or Firm—David A. Jackson

[57] ABSTRACT

An irrigating cannula fittable to a connecting pipe at the forward end of a handpiece and adapted to extract the lens nucleus for use in extracapsular cataract extraction, wherein a small-diameter tube extending from a fitting is provided with a flat insertion piece projecting laterally from the forward end of the tube and having a flow outlet which is open at the forward end of the piece and communicates with the channel of the tube, and a restraining piece extends from the connection of the base end of the insertion piece to the tube in a direction opposite to the insertion piece.

6 Claims, 10 Drawing Figures

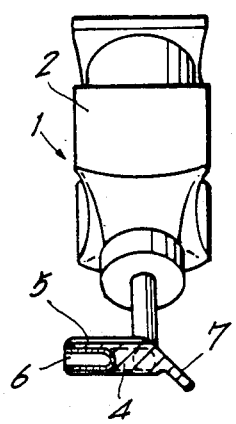
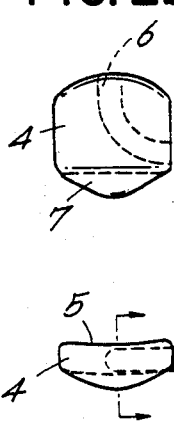
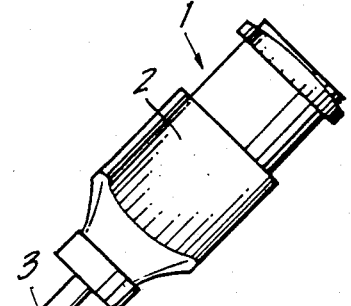
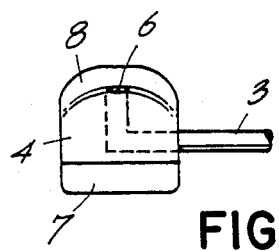
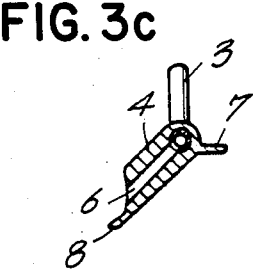
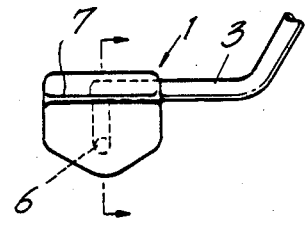

IRRIGATING CANNULA FOR EXTRACTING LENS NUCLEUS FOR USE IN EXTRACAPSULAR CATARACT EXTRACTION

BACKGROUND OF THE INVENTION

The present invention relates to an irrigating cannula for extracting the lens nucleus for use in extracapsular cataract extraction.

The lens is composed of lens cortex and lens nucleus which are made of lens fibers and fill up the lens capsule. The epithelium of the lens proliferates with age, and old epithelial cells collect in the center of the lens and become compressed, forming a lens nucleus of opaque sol in the form of a lens 6 to 9 mm in diameter. When opacities are formed in the path for light rays entering the pupil and travelling through the lens cortex and lens nucleus, serious visual impairment results which is a disease called a cataract.

The cataract is treated by removing the opaque lens and correcting the vision with a spectacle lens or contact lens or inserting an artificial lens as a substitute. The methods of removing the lens include intracapsular cataract extraction wherein the lens is entirely removed, and extracapsular cataract extraction wherein the anterior lens capsule, lens cortex and lens nucleus are removed with the posterior lens capsule only left unremoved.

Although inracapsular extraction was performed formally, extracapsular extraction is the primary practice in recent years for various reasons.

The present invention provides an irrigating cannula for removing the lens nucleus by extracapsular cataract extraction.

To remove the lens nucleus by extracapsular extraction, it has heretofore been practice to make an incision in the cornea, remove the anterior lens capsule and force out the lens nucleus from the lens cortex by applying pressure to the eyeball while lifting the cornea in accordance with the condition. With this method, the ophthalmologist and his assistant require skill in forcing out the lens nucleus smoothly. Moreover, since the lens nucleus is pushed out in frictional contact with the rear surface of the cornea by the pressure applied to the eyeball, there is a great likelihood that the cornea will be injured on the rear side.

As other methods, it is also known to directly scoop up the lens nucleus with a lens loop while dividing the lens cortex, or to directly contact a cryoprobe with the lens nucleus and withdraw the nucleus through a divided portion of the lens cortex, but because the lens cortex is a highly viscous gel, it is technically difficult to handle the lens nucleus or to attach the cryoprobe to the nucleus while dividing the lens cortex.

Especially if inserted through the lens cortex to an improper depth, the lens loop is likely to injure the posterior lens capsule by contact therewith.

SUMMARY OF THE INVENTION

An object of the present invention is to provide an irrigating cannula for extracting the lens nucleus easily without necessitating skill.

The irrigating cannula of the present invention is characterized in that the cannula comprises a small-diameter tube extending from a filling, a flat insertion piece attached to the forward end of the tube and directed laterally of the tube, the insertion piece being formed at its forward end with a flow outlet communicating with the forward end of the channel of the tube in communication with the fitting, and a restraining piece projecting from the connection of the base end of the insertion piece to the tube and directed in a direction opposite to the insertion piece.

To treat the patient with the irrigating cannula of the present invention, the anterior lens capsule is removed through an incision in the cornea, the forward end of the insertion piece is inserted into the lens cortex between the lens nucleus and the posterior lens capsule while allowing an irrigating liquid to flow out from the outlet, and the irrigating liquid is injected into the cortex with the outlet positioned under the lens nucleus. Since the liquid is injected into the lens cortex under the lens nucleus to fill the interior of the cortex, the lens nucleus is pushed up and led out along the upper surface of the insertion piece together with the irrigating liquid flowing out.

Unlike the conventional method of removing the lens nucleus, use of the irrigating cannula of the present invention makes it possible to spontaneously remove the lens nucleus merely by inserting the forward end of the insertion piece into the lens cortex without directly handling the nucleus, so that the present device has the great advantage of assuring extraction of the lens nucleus with ease and safety without necessitating skill. Whereas the conventional method is likely to injure the rear side of the cornea, use of the irrigating liquid greatly reduces the likelihood of injury.

BRIEF DESCRIPTION OF THE DRAWINGS

FIGS. 2 and 3 show irrigating cannulas embodying the invention and each include FIG. (a) which is a front view of the cannula, FIG. (b) which is a plan view of the same and FIG. (c) which is a view in section taken along the broken line in FIG. (a).

DETAILED DESCRIPTION OF THE INVENTION

Figure 1A:
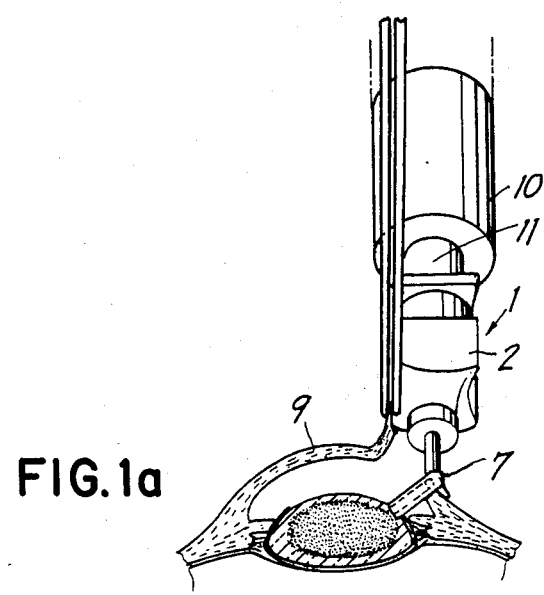
FIGS. 1 (a) to (d) are diagrams showing how an irrigating cannula is used for extracapsular cataract extraction.

FIG. 2 shows an embodiment of an irrigating cannula of the present invention. The irrigating cannula 1 comprises a fitting 2 fittable to the connecting pipe of a handpiece and a 19- to 20-gauge small-dimeter tube 3 (about 1 mm in outside diameter) connected to the fitting 2. The small-diameter tube 3 is bent at an angle of about 45° to 50° within a plane containing the central axis of the fitting 2. An insertion piece 4 extends from the forward end of the tube 3 at right angles with the plane containing the fitting and the tube. The insertion piece 4 is in the form of a flat plate 1.2 to 1.3 mm in thickness and is provided with a curved upper surface having a radius of curvature of about 20 mm and serving as a guide surface 5 for leading out the removed lens nucleus as will be described later. The channel of the small-diameter tube 3 has a base end communicating with the fitting 2 and a forward end bent through 90° in the interior of the insertion piece 4 and communicating with a flow outlet 6 formed in the forward end face of the insertion piece 4.

The insertion piece 4 has a short fin-like restraning piece 7 extending from the base end thereof in a direction opposite to the flow outlet 6 and formed on the lower side of the piece 4 at an obtuse angle of about 135° therewith.

FIG. 3 shows another embodiment wherein an insertion piece 4 attached to a small-diameter tube 3 is inclined at an angle of about 45° with respect to a plane containing a fitting 2 and the tube 3. A short guide piece 8 extends from the forward end of the insertion piece 4 on the lower part thereof, and a flow outlet 6 is open at the end face of the insertion piece 4 immediately above the guide piece 8.

The irrigating cannula of FIG. 2 can of course be provided with the guide piece 8 similarly.

Figure 1B:
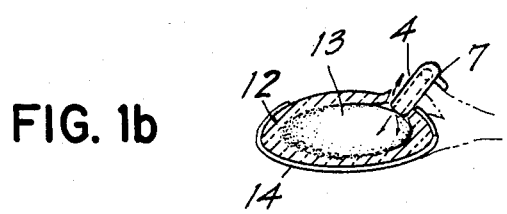
Figure 1C:
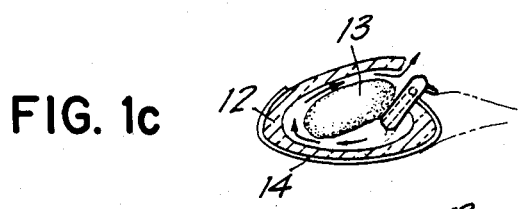
Figure 1D:
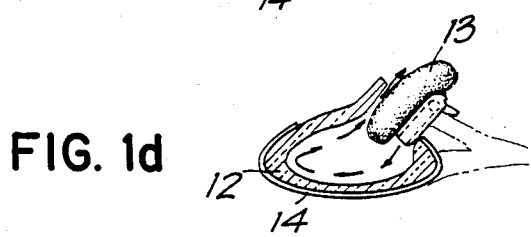

FIG. 1 shows how the irrigating cannula of the invention is used for treating a patient with a cataract. First, in the same manner as in the conventional method of extracapsular cataract extraction, the upper edge of the cornea 9 over the eyeball is incised in the form of a circular arc over a length of about ⅓ of the circumference, and the anterior lens capsule is removed.

The fitting 2 of the irrigating cannula 1 is fitted to a connecting pipe 11 of a cylindrical holder 10 such as a handpiece. The holder 10 is connected by a flexible tube to a tank containing physiological saline or like irrigating liquid and suspended at a level of about 75 cm above the operating table to cause the irrigating liquid to flow from the holder 10 through the small-diameter tube 3 of the cannula 1 and then flow out from the outlet 6 of the insertion piece 4. The doctor, standing close to the patient's head, inserts the insertion piece 4 of the cannula 1 into the lens cortex 12 from which the anterior capsule has been removed, between the lens nucleus and the posterior lens capsuel 14, by continueing irrigation while the cornea 9 is being lifted by himself or his assistant (FIG. 1 (a)).

The insertion piece 4 is inserted into the lens cortex 12 to a depth where the outlet 6 at the forward end of the piece 4 reaches the underside of the lens nucleus 13, and the irrigating liquid is injected into the lens cortex beneath the nucleus 13 (FIG. 1 (b)).

When the forward end of the insertion piece 4 is provided on the lower side thereof with the thin projecting guide piece 8 as shown in FIG. 3, the insertion piece 4 can be inserted into the lens cortex with greater ease, while the liquid flow forced out from the outlet 6 can be effectively concentrated under the nucleus 13. Further because the insertion piece 4 has the restraining piece 7 projecting from its base end, the depth to which the piece 4 is inserted into the lens cortex can be limited by the contact of the restraining piece 7 with the edge of the cornea. This eliminates the objection that the insertion piece 4 will injure the posterior lens capsule 14 when inserted too deep or the irrigating liquid will be applied from the outlet 6 which has not reached the underside of the lens nucleus 13 owing to insufficient insertion.

The restraining piece 7 serves to ease extraction of lens nucleus 13 by applying light pressure on cornea sclera.

When the cannula 1 is held with its insertion piece 4 positioned under the lens nucleus 13 for continued irrigation, the irrigating liquid collects under the nucleus 13 and flows out from the cortex at one side thereof where the insertion piece 4 is inserted (FIG. 1 (b)). Since the irrigating liquid collecting in the interior of the lens cortex 12 has a high pressure and blocked by the lens nucleus, the nucleus is pushed up by the liquid pressure and starts to move toward insertion side where the pressure is lower (FIG. 1 (c)).

Since the irrigating liquid flows out while washing the upper surface of the insertion piece 4, the lens nucleus 13 floats, rides on the insertion piece 4 with the liquid and is led out by the pressure of the irrigating liquid (FIG. 1 (d)).

After the lens nucleus has been extracted from the cortex 12, the cortex is aspirated and removed by a cortex aspirator.

The posterior lens capsule 14 is thereafter ground to remove all remaining portions of the cortex from its surface. An artificial lens is placed on the posterior capsule when required, and the cornea is sutured to complete the operation.

According to the present invention, the lens nucleus is spontaneously led out by liquid pressure and removed merely by inserting the insertion piece of the irrigating cannula into the cortex. The cannula is therefore easy to use and requires little or no skill.

Moreover, the irrigating liquid flowing out from the cortex serves as a lubricant for the movement of the lens nucleus to eliminate the likelihood of injuring the cornea. Thus, the present device has various great advantages.

What is claimed is:

1. An irrigating cannula for extracting a lens nucleus in an extracapsular cataract extraction while providing a flow of irrigating liquid, said cannula comprising;
   (a) a connector having a bore extending centrally therethrough;
   (b) a small-diameter tube, the small-diameter tube having a bore extending therethrough, the tube having a proximal end secured to the connector and in fluid communication with the connector, the small-diameter tube having a distal end extending outwardly from the connector;
   (c) an insertion piece attached to the distal end of the tube, the insertion piece extending both forwardly and laterally from the tube, to form a planar surface;
   (d) the insertion piece having a base end attached to the small-diameter tube, a front end comprising a forward surface, a lateral side surface located between the front end and the base end, and an upper planar surface extending between the base end and the front end of the insertion piece;
   (e) a bore within the insertion piece, the insertion piece bore extending from the base end of the insertion piece and in fluid communication with the bore of the small-diameter tube, the insertion piece bore having a lateral outlet on the lateral side surface of the insertion piece;
   (f) a restraining piece provided at the base end of the insertion piece, the restraining piece projecting at an angle in the range of between 180 and 270 degrees to the planar upper surface of the insertion piece;
   (g) the restraining piece serving to limit the extent to which the insertion piece is inserted beneath the nucleus and to apply a slight pressure on the sclera for easy delivery of the lens nucleus.

2. An irrigating cannula as defined in claim 1 wherein the small-diameter tube is slightly bent between the connector and the insertion piece, and the insertion piece projects approximately at right angles with a plane containing the bent small-diameter tube.

3. An irrigating cannula as defined in claim 1 wherein the small-diameter tube is slightly bent between the connector and the insertion piece, and the insertion projects obliquely with respect to a plane containing the small-diameter tube.

4. An irrigating cannula as defined in claim 1 wherein the insertion piece is provided with a guide piece projecting from its front end at a lower side of the insertion piece bore.

5. An irrigating cannula as defined in claim 2 wherein the insertion piece is provided with a guide piece projecting from its front end at a lower side of the insertion piece bore.

6. An irrigating cannula as defined in claim 3 wherein the insertion piece is provided with a guide piece projecting from its front end at a lower side of the insertion piece bore.

* * * * *